(12) United States Patent
Chavez et al.

(10) Patent No.: US 10,161,924 B2
(45) Date of Patent: Dec. 25, 2018

(54) SENSOR SYSTEM THAT USES EMBEDDED OPTICAL FIBERS

(71) Applicant: National Technology & Engineering Solutions of Sandia, LLC, Albuquerque, NM (US)

(72) Inventors: Marcus Alexander Chavez, Rio Rancho, NM (US); Timothy T. Covert, Albuquerque, NM (US); Michael David Willis, Edgewood, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 174 days.

(21) Appl. No.: 14/599,901

(22) Filed: Jan. 19, 2015

(65) Prior Publication Data

US 2015/0268216 A1 Sep. 24, 2015

Related U.S. Application Data

(60) Provisional application No. 61/969,593, filed on Mar. 24, 2014.

(51) Int. Cl.
*G01N 21/01* (2006.01)
*G01N 33/22* (2006.01)
*G01D 5/26* (2006.01)
*G01N 21/17* (2006.01)
*G01N 21/45* (2006.01)
*G01P 3/36* (2006.01)

(52) U.S. Cl.
CPC .......... *G01N 33/227* (2013.01); *G01D 5/268* (2013.01); *G01N 21/17* (2013.01); *G01N 21/45* (2013.01); *G01N 2201/06113* (2013.01); *G01N 2201/088* (2013.01); *G01N 2201/0846* (2013.01); *G01P 3/36* (2013.01)

(58) Field of Classification Search
CPC ..................................................... G01N 21/01
USPC ....... 422/82.05, 82.06, 82.09, 82.11; 436/43, 436/164; 356/450, 477
See application file for complete search history.

(56) References Cited

U.S. PATENT DOCUMENTS 4,560,881 A * 12/1985 Briggs ................... G01N 21/64
250/458.1
4,564,598 A * 1/1986 Briggs ............... G01N 21/6428
250/459.1

(Continued)

*Primary Examiner* — Brian J. Sines
(74) *Attorney, Agent, or Firm* — Medley, Behrens & Lewis, LLC; Samantha Updegraff

(57) ABSTRACT

Sensor systems including an interferometer system are disclosed herein. In a general embodiment, the sensor system includes an optical fiber that is embedded into a sample, where the optical fiber has a reflective tip. The optical fiber is optically coupled to a sensor and a detector of the laser interferometer system. The sensor system further includes a computing device or circuit that is configured to receive electrical signals generated by the detector. The laser source is configured to emit light, which is coupled into the optical fiber. The light travels through the optical fiber until the light reaches the reflective tip, where it is reflected back through the optical fiber. The detector is impacted by the reflected light, and generates an electrical signal based upon the reflected light. The computing device generates a value that is indicative of a behavior of the sample based upon the electrical signal.

12 Claims, 9 Drawing Sheets

(56) References Cited

U.S. PATENT DOCUMENTS

| | | | | |
|---|---|---|---|---|
| 4,573,761 | A * | 3/1986 | McLachlan | G01N 21/65 356/301 |
| 5,023,845 | A | 6/1991 | Crane et al. | |
| 5,059,790 | A * | 10/1991 | Klainer | G01N 21/7703 250/227.21 |
| 5,106,387 | A * | 4/1992 | Kittrell et al. | 606/15 |
| 5,187,983 | A | 2/1993 | Bock et al. | |
| 5,436,454 | A * | 7/1995 | Bornstein | G01N 21/552 250/339.07 |
| 5,452,087 | A | 9/1995 | Taylor et al. | |
| 5,596,409 | A * | 1/1997 | Marcus et al. | 356/479 |
| 5,600,070 | A * | 2/1997 | Wlodarczyk | 73/715 |
| 5,714,680 | A | 2/1998 | Taylor et al. | |
| 5,841,545 | A * | 11/1998 | Young | G01K 11/00 356/436 |
| 5,862,273 | A * | 1/1999 | Pelletier | G01N 21/65 356/301 |
| 5,892,860 | A * | 4/1999 | Maron et al. | 385/12 |
| 5,925,879 | A | 7/1999 | Hay | |
| 6,016,702 | A * | 1/2000 | Maron | 73/705 |
| 6,205,272 | B1 * | 3/2001 | O'Rourke et al. | 385/33 |
| 6,571,639 | B1 | 6/2003 | May et al. | |
| 6,597,820 | B1 | 7/2003 | Sheem | |
| 7,728,982 | B2 | 1/2010 | Tan et al. | |
| 2007/0006663 | A1 * | 1/2007 | Zerwekh | G01K 11/3206 73/800 |
| 2008/0319382 | A1 * | 12/2008 | Blank | A61B 5/14532 604/66 |
| 2012/0210797 | A1 | 8/2012 | Yu et al. | |
| 2013/0256534 | A1 * | 10/2013 | Micheels | G01N 21/255 250/339.07 |
| 2013/0265568 | A1 * | 10/2013 | Micheels | G01N 21/359 356/51 |
| 2014/0171936 | A1 | 6/2014 | Govari et al. | |
| 2014/0299753 | A1 | 10/2014 | Pan et al. | |

* cited by examiner

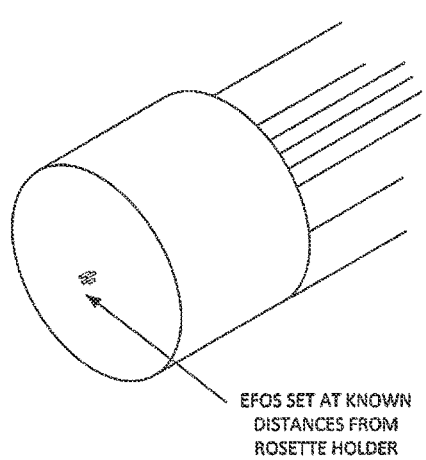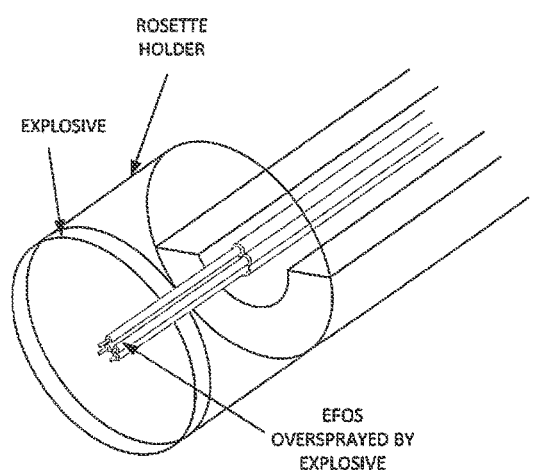
FIG. 7
FIG. 8

SENSOR SYSTEM THAT USES EMBEDDED OPTICAL FIBERS

RELATED APPLICATION

This application claims priority to U.S. Provisional Patent Application No. 61/969,593, filed on Mar. 24, 2014, and entitled "EMBEDDED FIBER OPTIC SENSORS FOR MEASURING TRANSIENT DETONATION/SHOCK BEHAVIOR", the entirety of which is incorporated therein by reference.

STATEMENT OF GOVERNMENTAL INTEREST

This invention was developed under Contract DE-AC04-94AL85000 between Sandia Corporation and the U.S. Department of Energy. The U.S. Government has certain rights in this invention.

BACKGROUND

Acquiring information about a sample prior to a product being deployed is often highly desirable. For example, it is critical to understand how a portion of an airplane wing deforms when subjected to external forces. In another example, it is critical to understand how a material that is to be used in a bridge will respond to particular conditions. In still yet another example, it is desirable to understand properties of an explosive material during detonation, thereby allowing for an explosive to be properly designed for a particular application.

With more detail pertaining to explosives, energetic materials (explosives) research has led to an increased interest in miniaturization of energetic base components (e.g., to microscale sizes). As the energetic base components have reduced in size, a desire for probing behavior that occurs in explosives (during detonation) on the microscale has emerged. Further, more generally, there has been an increased interest in dynamic pressure loading of inner materials. Conventional diagnostics that measure these events are relatively large and typically do not allow for unobtrusive interrogation of physical phenomena of interest in microscopic components or experimental configurations.

In a non-limiting example with reference to explosives, it is desirable to ascertain velocity of a reaction front that propagates from a particular location in the explosive. Existing techniques for ascertaining such velocity require a relatively large amount of explosive material, where measurement devices are placed on the explosives, such as time of arrival devices (TOADS). TOADS are configured to output data that is indicative of the velocity of the reaction front. For some applications and materials, however, use of such a large amount of explosive material does not correlate with practical use of the explosive material (e.g., having a thickness on the order of microns).

SUMMARY

Technologies pertaining to generating data that is indicative of behavior of a sample of interest are disclosed herein. In a general embodiment, a sensor system described herein is configured to compute a value that is indicative of a behavior of a sample. For instance, the sample may be an explosive, such as a light-initiated high explosive (LIHE), where an explosive reaction is initiated responsive to the LIHE being impacted by relatively high intensity light. An exemplary LIHE is silver acetylide-silver nitrate (SASN). For instance, a material that comprises SASN can be coated on a target, where thickness of the material is on the order of microns (e.g. 10-200 µm). The sensor system also includes an optical fiber that is embedded in the sample (referred to as an embedded optical fiber (EOF)). The EOF has an inner fiber within which light travels, and further has a planar end that is cleaved orthogonal to the inner fiber. The cleaved end has a mirrored surface applied thereto, such that light that travels in the inner fiber is reflected back through the inner fiber by the mirrored surface. Thus, the mirrored surface of the cleaved end of the EOF prevents light from escaping the EOF. In an example, the mirrored surface is arranged in parallel with an exposed surface, and is positioned at a depth in the sample relative to the exposed surface.

In an embodiment, the sensor system described herein also includes a laser interferometer system that comprises a light source (e.g., laser source) and a detector. Both the laser source and the detector of the laser interferometer system are optically coupled to the optical fiber. The sensor system also includes a computing device that is in communication with the detector of the laser interferometer system.

In operation, the laser source is controlled to emit light, which is directed to the inner fiber of the EOF. The light travels in the inner fiber along a length of the EOF and is reflected by the mirrored surface at the cleaved end of the EOF. The detector, being optically coupled to the optical fiber, is impacted by the light reflected from the mirrored surface of the cleaved end of the EOF. The detector is configured to convert the light into an electrical signal, and the computing device receives such electrical signal. The computing device is configured to compute a value that is indicative of a behavior of the sample based upon the electrical signal. The behavior can refer to a reaction of the sample responsive to being subject to an external force, a stimulant, or the like. For instance, when the sample is an explosive, the laser source can be controlled to emit light during detonation of the explosive. During detonation, a reaction wavefront propagates through the sample, resulting in application of force on the EOF, thereby moving or deforming the cleaved end of the optical fiber. This alteration to the EOF causes a property of the reflected light to change (e.g., a Doppler shift is induced), wherein the change is indicative of a behavior of the sample (e.g., velocity of the reaction front, internal pressure loading, etc.

Additional features and advantages are described herein, and will be apparent from the following Detailed Description and the figures.

BRIEF DESCRIPTION OF THE DRAWINGS

FIG. 7 is an isometric view of an exemplary device with optical fibers embedded therein.

FIG. 8 is a transparent view of the device shown in FIG. 7.

DETAILED DESCRIPTION

Figures 1, 2:
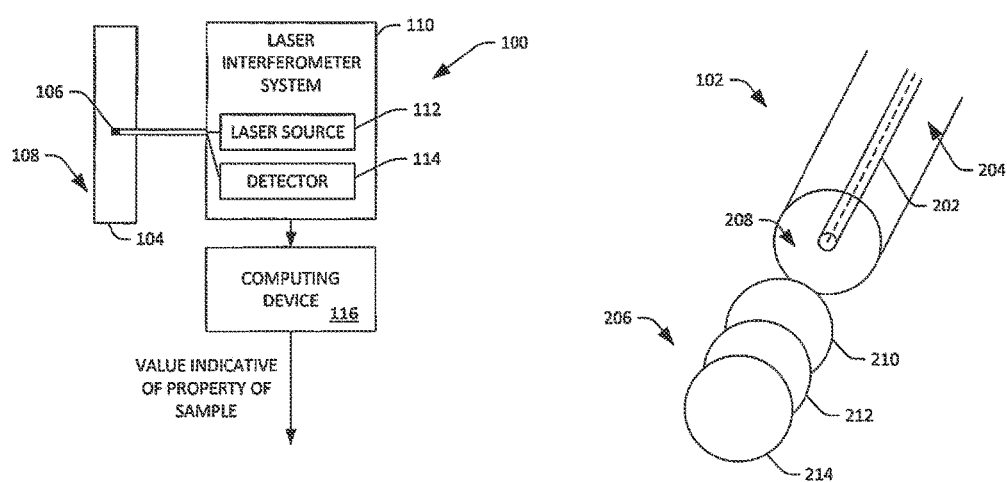
FIG. 1 is a functional block diagram of an exemplary sensor system.
FIG. 2 is an exploded view of an optical fiber.

Technologies pertaining to a sensor system that is configured to generate data indicative of at least one behavior of a sample are disclosed herein. With reference now to FIG. 1, in a general embodiment, a system 100 is illustrated. As will be described in greater detail herein, the sensor system 100 is well-suited to compute values that are indicative of one or more behaviors of a sample. With more particularity, the sensor system 100 is particularly well-suited to compute values that are indicative of one or more behaviors of a thin sample (e.g., a sample having a thickness on the order of 10-200 μm). It can be ascertained, however, that the sensor system 100 can be used to compute values of properties of much thicker samples.

The system 100 includes an optical fiber 102 that is embedded in a sample 104. The optical fiber 102 will be referred to herein as an embedded optical fiber (EOF). The sample 104 can be or include a variety of different material types, sizes, and shapes. For example, the sample 104 may be a layer of material included in a wing of an airplane. In another example, the sample 104 may be a portion of metal used in a bridge. In still yet another example, the sample 104 may be an explosive, such as a light-initiated high explosive (LIHE). In a non-limiting example, the LIHE can be silver acetylide-silver nitrate (SASN), which can be coated onto a substrate. In such an example, thickness of the explosive can be on the order of microns, such as between 10-500 microns. In another example, thickness of the explosive can be between 100 microns and 1 mm.

The EOF 102 has an inner fiber (not shown) within which light travels. The EOF 102 also has a planar end that is cleaved orthogonal to the inner fiber of the EOF 102. Additionally, the cleaved end has a mirrored surface 106 applied thereto, such that light traveling in the inner fiber of the EOF 102 is reflected back through the inner fiber responsive to the light impacting the mirrored surface 106. In a non-limiting example, as will be shown and described below, the mirrored surface 106 can include one or more types of material, such as aluminum, titanium, etc. As shown in FIG. 1, the mirrored surface 106 can be positioned in parallel to an exposed surface 108 of the sample 104. Further, the mirrored surface 106 may be embedded in the sample 104 at a desired depth, such that mirrored surface 106 is at a desired distance from the exposed surface 108 of the sample 104.

The system 100 also includes a laser interferometer system 110. The laser interferometer system 110 includes a laser source 112 and a detector 114. Both the laser source 112 and the detector 114 are optically coupled to the EOF 102; thus, light emitted by the laser source 112 is directed to the inner fiber of the EOF 102 towards the cleaved mirrored surface 106. The detector 114 is configured to receive light emitted by the laser source 112 that is reflected off of the mirrored surface 106 of the EOF 102.

The system 100 additionally comprises a computing device 116 that is in communication with the detector 114, and is configured to receive signals generated by the detector 114. For instance, the computing device 116 can be electrically coupled to the detector 114, in wireless communication with the detector 114, etc. The computing device 116 can be any suitable computing device, such as a digitizer, a desktop computing device, a laptop computing device, a tablet (slate) computing device, a mobile telephone, a wearable computing device, or the like.

In operation, the laser source 112 is controlled to emit laser light, which is directed to the inner fiber of the EOF 102. The laser light travels in the inner fiber until the laser light reaches the mirrored surface 106, and the mirrored surface 106 reflects the laser light back through the inner fiber of the EOF 102. The detector 114 is impacted by the reflected light and generates an electrical signal that is based upon the light that impacts the detector 114. The computing device 116 receives the electrical signal emitted by the detector 114 and outputs a value that is indicative of a behavior of the sample 104 based upon such electrical signal.

Generally, the sensor system 100 can be configured to compute values that are indicative of a variety of behaviors of a sample. For instance, the computing device 116 can be configured to output a value that is indicative of internal pressure at the mirrored surface 106 of the EOF 102 over time (e.g., when subjected to an external force, when undergoing a reaction, etc.). In another example, the computing device 116 can be configured to compute a value that is indicative of velocity of a reaction front that propagates through the sample 104 (e.g., when the sample 104 is an explosive).

The sensor system 100 has various advantages over conventional sensor systems. For instance, the EOF 102 is relatively small, such that is can be embedded into the sample 104 without impacting a measurement obtained by the sensor system 100. In contrast, conventional sensor systems tend to be relatively large, where attachment of devices that are used to obtain the measurement to the sample 104 perturbs the measurement. Further, while not shown, the sensor system 100 can include multiple EOFs, where tips (cleaved ends) of the EOFs are placed at different depths in the sample 104. Conventional diagnostic systems are too large to allow for such a "stepped" configuration.

Turning now to FIG. 2, an exploded isometric view of the EOF 102 is illustrated. The EOF 102 has an inner fiber 202 that is made of fused silica having an index of refraction. The EOF 102 also comprises cladding 204 that symmetrically surrounds the inner fiber 202. In an example, the cladding 204 can be made of fused silica having an index of refraction that is less than the index of refraction of the inner fiber 202.

The EOF 102 also comprises a spectral (e.g., mirrored) surface 206 adhered to a cleaved end 208 of the EOF 102. As shown, the spectral surface 206 can be made of three separate layers, a first layer 210 of titanium, a second layer 212 of pure aluminum, and a third layer 214 made of aluminum oxide. The first layer 210 can be physical vapor deposited onto the cleaved end 208 of the EOF 102, the second layer 212 can be physical vapor deposited onto the first layer 210, and the third layer 214 can be physical vapor deposited onto the second layer 212. For example, the first layer 210 can act as an adherent between the cleaved end 208 of the EOF 102 and the second layer 212. The third layer 214 can act as a protective layer for the second layer 212 (the aluminum).

While the spectral surface 206 is illustrated as including multiple layers, it is to be understood that the spectral surface 206 may include more or fewer layers. For instance, the spectral surface 206 may be made of a single aluminum layer.

Figure 3:
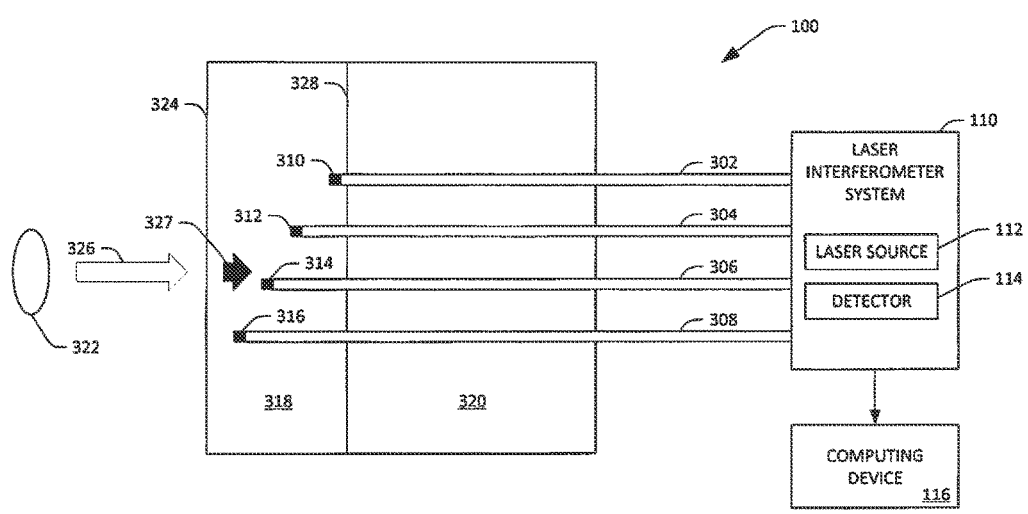
FIG. 3 is a functional block diagram of an exemplary sensor system.

Now referring to FIG. 3, an exemplary sensor system 300 is illustrated. The sensor system 300 comprises a plurality of EOFs 302-308 that have respective cleaved ends with reflective surfaces 310-316 applied to the cleaved ends. The reflective surfaces 310-316 of the EOFs 302-308 are embedded into a sample 318. For instance, the sample 318 may be a LIHE. Further, the reflective surfaces 310-316 of the EOFs 302-308 can be embedded at different depths in the sample 318.

To embed the reflective surfaces 310-316 of EOFs 302-308 in the sample 318, the EOFs 302-308 can protrude from a surface of a target 320, which can be made of, for example, a metal. When the reflective surfaces 310-316 of the EOFs 302-308 are appropriately displaced relative to a front surface of the target 320, the sample 318 can be applied over the front surface of the target 320. This results in the mirrored surfaces 310-316 of the EOFs 302-308 being embedded in the sample 318. As shown, the mirrored surfaces 310-316 are arranged in parallel to the front surface of the sample 318, and embedded in the sample at different depths in the sample 318 relative to the front surface of the sample 318.

The system 300 additionally includes the laser interferometer system 110 and the computing device 116. The laser interferometer system 110 includes the laser source 112 and the detector 114, wherein the EOFs 302-308 are optically coupled to the laser source 112 and the detector 114.

In operation, the laser source 112 is configured to emit laser light that is directed (e.g., through splitters) to inner fibers of the EOFs 302-308. The laser light travels the length of the EOFs 302-308 until the light is reflected from the reflective surfaces 310-316, which directs the light in the opposite direction in the inner fiber. Detectors are configured to detect the reflected light and generate electrical signals based upon the reflected light. The computing device 116 receives the electrical signals emitted by the detectors, and computes a value indicative of a behavior of the sample 318.

When the sample 318 is a LIHE, a light source 322 can be caused to direct relatively high intensity light to an exposed surface 324 of the sample 318. This light is represented by arrow 326 in FIG. 3. The light initiates a reaction in the sample 318, and a reaction front propagates in the direction of arrow 327 towards an inner surface 328 of the sample 318. As the reactive front moves in the direction of the arrow 327, the reflective surface 316 is perturbed, creating, for example, a Doppler shift in the light reflected by the reflective surface 316. Subsequently, the reactive front moves further in the direction of the arrow 327, resulting in perturbation of the reflective surface 314 (which results in a Doppler shift of the light reflected by the reflective surface 314). Over time, as the reaction front propagates towards the inner surface 328, the reflective surfaces 312 and 310 will be perturbed. Detectors in the laser interferometer system 110 (including the detector 114) can output electrical signals based upon light signals that impact such detectors. The computing device 116 can output values that are indicative of behavior of the sample 318 during detonation. For instance, the computing device 116 can be configured to output apparent particle velocities corresponding to light reflected in the EFOs 302-308, which in turn can be used to estimate velocity of the reaction front through the sample 318. Values of other properties can also be computed, such as internal pressure at the locations in the sample 318 of the reflective surfaces 310-316 of the EFOs 302-308.

Figure 4:
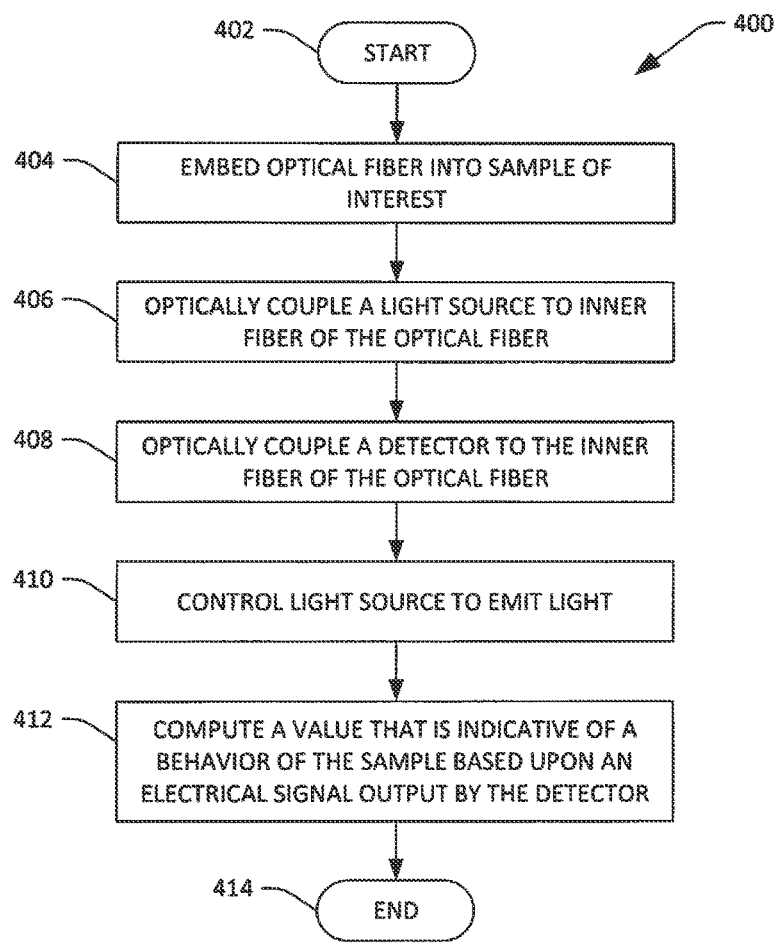
FIG. 4 is a flow diagram that illustrates an exemplary methodology for generating a value that is indicative of a behavior of a sample.
Figure 5:
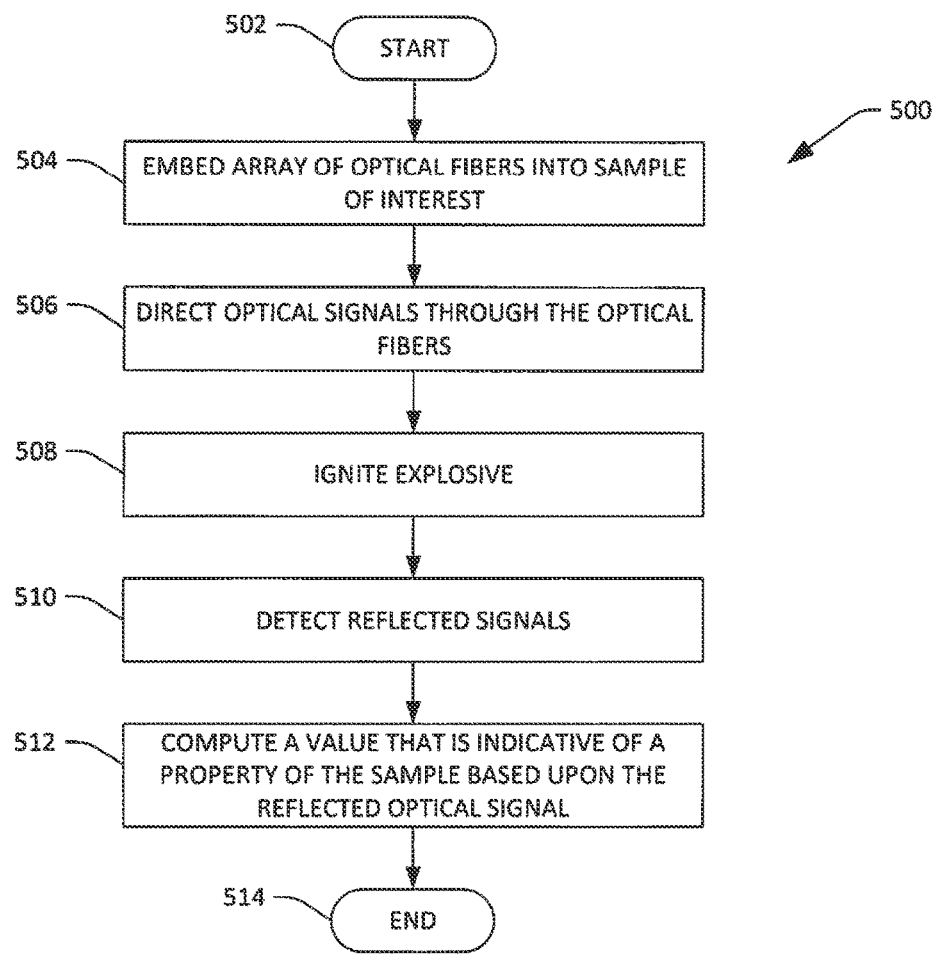
FIG. 5 is a flow diagram that illustrates an exemplary methodology for generating a value that is indicative of a behavior of an explosive.

FIGS. 4 and 5 illustrate exemplary methodologies relating to generating values indicative of a behavior of a sample. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, one or more of the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring to FIG. 4, an exemplary methodology 400 that facilitates computing a value that is indicative of a behavior (e.g., property) of a sample is illustrated. The methodology 400 starts at 402, and at 404, an optical fiber is embedded into a sample of interest. As described above, the optical fiber can include an inner fiber through which light travels. Further, the optical fiber has a planar end that is cleaved orthogonal to the inner fiber, and the cleaved end has a reflective surface adhered thereto. At 406, a light source (laser source) is optically coupled to the inner fiber, and at 408, a detector is optically coupled to the inner fiber. At 410, the light source is controlled to emit light, wherein the light emitted by the light source travels in the inner fiber and reflects off of the reflective surface adhered to the cleaved end of the inner fiber. The reflected light impacts the detector, and the detector generates an electrical signal based upon the light that impacts the detector. At 412, a value that is indicative of a behavior of the sample over time is computed based upon the electrical signal generated by the detector. The methodology 400 completes at 414.

Now referring to FIG. 5, an exemplary methodology 500 that facilitates computing a value that is indicative of a behavior of an explosive during detonation is illustrated. The methodology 500 starts at 502, and at 504, an array of optical fibers is embedded into a sample of interest. As noted above, the array of optical fibers can be embedded such that tips of the optical fibers are embedded at different depths in the explosive (e.g., relative to an exposed surface of the explosive).

At 506, optical signals are directed through the optical fibers, and at 508, the explosive is ignited. At 510, reflected signals impact detectors, and the detectors output electrical signals based upon the reflected light signals that impact the detectors. At 512, a value that is indicative of a property of the explosive is computed based upon the electrical signals. As noted previously, this behavior may be velocity of a reaction front that propagates through the explosive, pressure applied to the optical fibers at their tips, etc. The methodology 500 completes at 514.

EXAMPLES

By way of example and not limitation, the following examples are illustrative of various embodiments of the present disclosure.

A sensor system was developed that comprises a laser interferometry system referred to as a photonic Doppler velocimetry (PDV) interferometer. The PDV was coupled with EFOs to measure transient explosive and shock/non-shock behavior. Typical names for explosive transient behavior are deflagration to detonation transition (DDT) and build-up of detonation (BUD). The sensor system was used to measure apparent particle velocity at several locations in LIHEs, wherein the primary explosive in the LIHEs was SASN. Historically, detonation velocity of SASN-based explosives have been measured in the conventional manner described above, where a relatively long strip of the explosive is initiated on one end and time of arrival (TOA) pins are located on the explosive at known distances (e.g., usually several inches) from the ignition point. In conventional systems, measurements range from 0.5 to 1.5 mm/μs for areal densities ($\rho_{AD}$) of SASN explosive ranging from 11.4 to 118.8 mg/cm². This type of measurement is well-suited for determining steady state sweeping waves, but neglects the nearly one-dimensional unsteady wave propagation a LIHE can offer on the order of hundreds of microns or less, since an LIHE ignites from an exposed outer surface and burns towards the substrate onto which the LIHE is spray deposited.

A first test of the sensor system described herein produced outcomes that indicated that orientation of the fiber tip (the mirrored surface) is desirably perpendicular to the incoming deflagration, detonation, or shockwave. This is due to the reflection of the reactive wavefront with the fiber tip being maximized when the mirrored surface applied to the cleaved planar tip is perpendicular to the above-mentioned incoming deflagration, detonation, or shockwave. In order to effectively measure the deflagration/detonation velocity of SASN-based LIHEs, in the test, four fibers were placed adjacent to one another in a rosette arrangement at several positions along the reactive wavefront propagation axis.

Example 1: Laser Interferometer

As described above, a sensor system in accordance with the features described herein includes a laser interferometer system. In tests, the laser interferometer was a PDV, which uses the Doppler-shifted light reflected from a moving source (spectral or diffuse reflective surface) combined with non-Doppler-shifted light emitted from a stationary reference to create an interference or beat frequency. The velocity, such as the particle velocity of the reflective surface, is proportional to the beat frequency. By using a reference light source with a different frequency than the measurement light source, a beat frequency was created with a non-moving reflective surface, yielding diagnostic advances. This "up shifted" technique was achieved through use of a tunable laser, although a Bragg crystal acousto-optic amplifier could also be used. The sensitivity for the detectable amount of displacement was half the wavelength of the laser source for a minimum time that the detector and digitizer could detect with a sufficiently large signal-to-noise ratio.

The PDV in the tested sensor system had a 1550 nm wavelength infrared laser, which could detect 775 nm of normal displacement (assuming no change in index of refraction) from a spectral surface. An apparent change in the position of the spectral surface can be produced by a change in the index of refraction of the medium the laser light is traveling through. This can result in the optical path length change of 775 nm, but this is only an apparent change and not the actual length of the medium. The optical effects stem from mechanical and thermal inputs into the fiber system. Bending the fibers produces in apparent particle velocity shift, as does thermal expansion or contraction of the fiber. Thus, as indicated previously, the utilization of optical fibers, in the manner described above, can be employed for different environments other than explosives.

The infrared detectors of the PDV had a 2 GHz bandwidth, and the digitizers had 2.5 GHz bandwidth. An up-shifted PDV system using a fixed acousto-optic amplifier at 500 MHz had a working range of measurable velocities from less than 0.01 m/s to 387.5 m/s, so long as the signal to noise ratio was greater than 1, especially in the low velocity regime. Greater velocity ranges are achievable with a higher frequency acousto-optic amplifier or using a tunable laser for the reference source. Power output near the fiber tip was on the order of 10 mW to 50 mW, and was not able to ignite the sensitive primary explosive prior to the ignition source applying high intensity light to the exposed surface of the explosive. The power output at the tip was dependent on bending of the fibers, coating quality, laser interferometer output, etc.

Example 2: Optical Fibers

Figure 6:
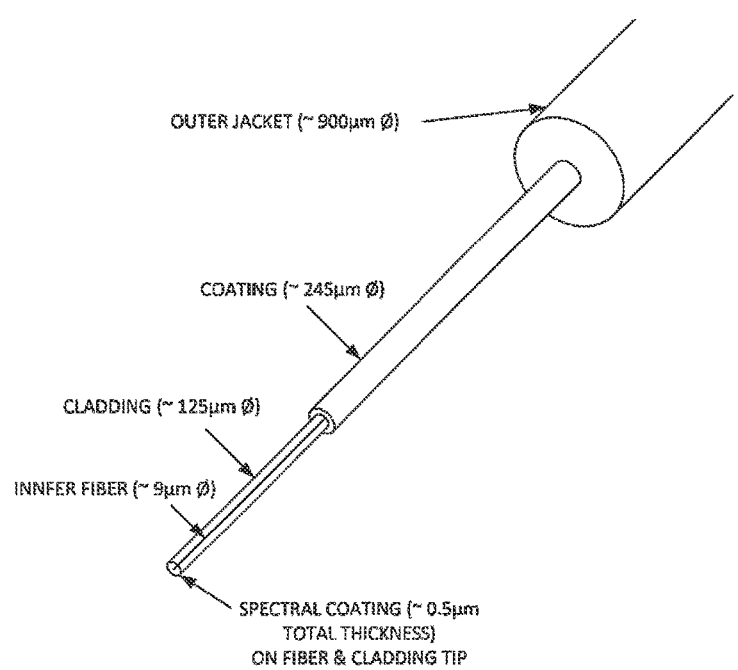
FIG. 6 is an isometric view of an exemplary optical fiber.

The optical fibers were manufactured using plain cleaved Corning SMF-28 9/125 μm diameter fibers. In an example, a coating of 4000 Å aluminum was physically vapor-deposited to achieve the spectral coating on the plain cleaved tip. Subsequently, in other experiments, optical fibers had a coating of 3500 Å thick aluminum spectral surface over a 500 Å titanium layer for adherence to the fiber tip. Over the aluminum was a 1000 Å layer of aluminum oxide to act as a protective coating. A 25.4 mm segment of fiber jacket was cut away to expose the coated fiber tip for use in the experiments. FIG. 6 illustrates an exemplary optical fiber used in the experiments.

Figure 9:
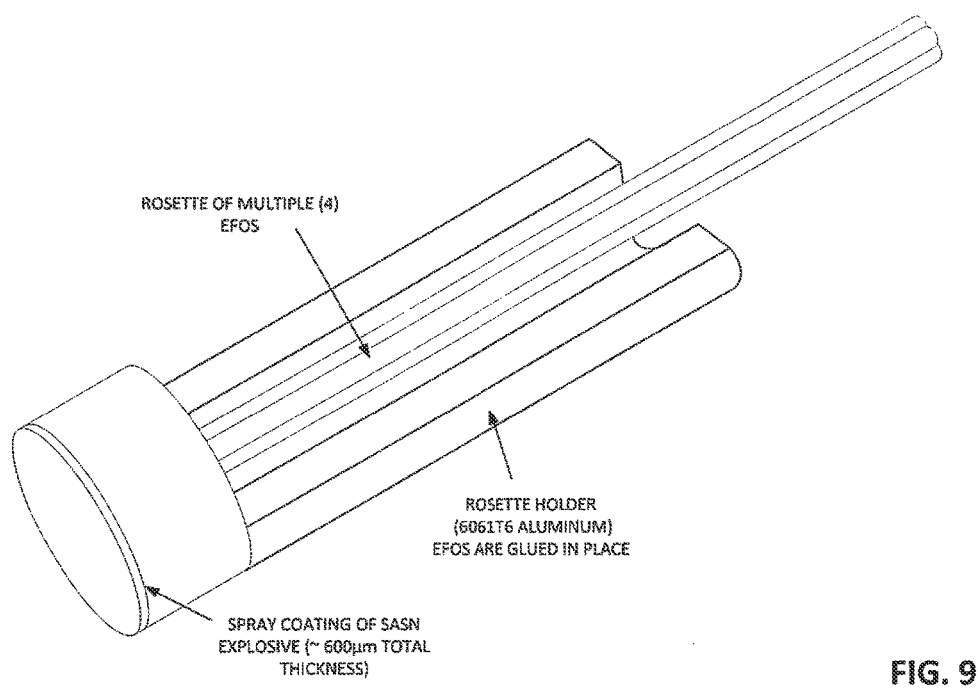
FIG. 9 is an isometric view of the device shown in FIGS. 7 and 8 with a coating of light-initiated high explosive (LIHE) applied thereto.

The completed fibers were then installed into a probe holder. FIGS. 7-9 illustrate isometric views of the exemplary probe holder with an array of optical fibers installed therein. FIGS. 8 and 9 illustrate an explosive coated onto the probe, such that array of optical fibers are embedded in the explosive. An optical comparator and laser alignment tools were used to achieve desired locations of tips of the optical fiber relative to the probe surface and to each other. The accuracy of using the optical comparator was on the order of +/−2 μm. Better diagnostics can be used to position the fibers in future experiments, as well as capture distance between fiber tips. The actual fiber optic was composed of fused silica batched and drawn at DuPont® with a 9 μm inner core diameter and outer core diameter measured at 121-130 μm. Since the fiber diameter had some amount of range associated with it, it was prudent to measure the diameter to ensure proper accounting for rarefaction effects in the future.

Example 3: Mode of Detection

Figure 10:
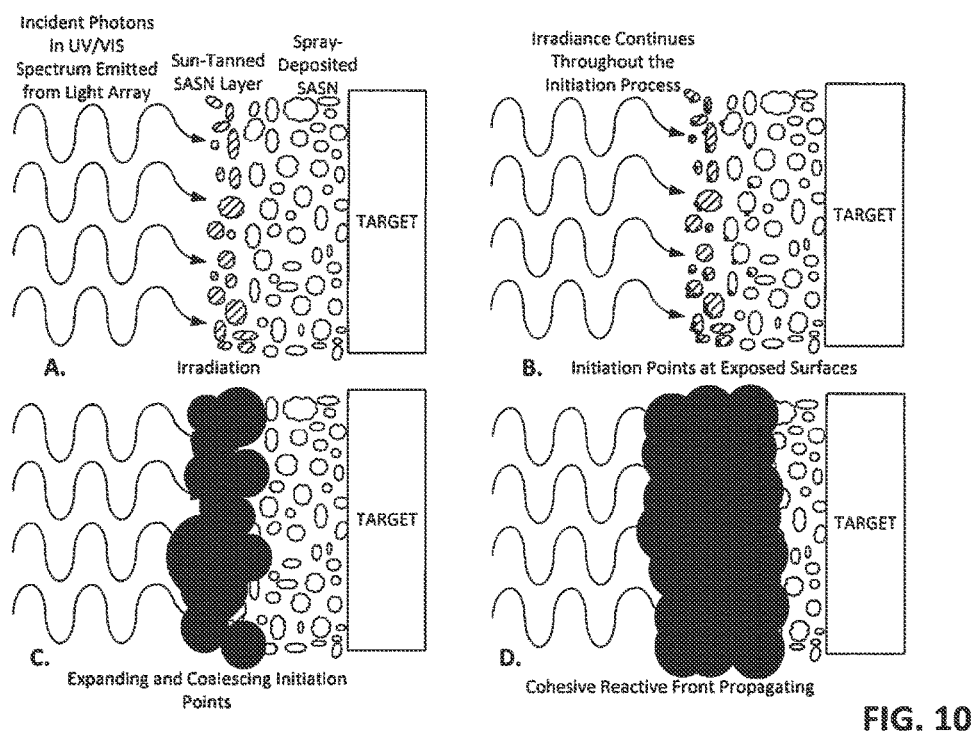
FIG. 10 illustrates a propagated explosive front (A-D).

Initially, noninvasive time of arrival devices (TOADS) were introduced to measure the actual deflagration and/or detonation velocity produced by light-initiated SASN explosive at several locations within the reaction flow. The fibers needed to be placed in close proximity to each other, no longer than the total thickness of the explosive coating, to avoid multidimensional reactive wavefronts. The reasoning behind this rule of thumb is as follows: ignition occurs at many points near the exposed surface, and such points eventually coalesce into a cohesive reaction front some distance into the unreacted explosive. FIG. 10 describes, step-by-step (A-D), the issue with using a single probing point in a real explosive upon ignition. Since the LIHE type of experiment is only quasi-one-dimensional, the interpretation of data became difficult with single probing points along the flow. Thus, larger arrays with multiple probes at each depth within the explosive would be more representative of the non-steady reaction wavefront propagation.

The TOA timing resolution achieved with the sensor system on SASN explosive exceeded any previously reported timing resolution for SASN using conventional diagnostic systems. Besides resolving TOA data, the probes produced apparent particle velocity traces. The apparent particle velocity time history produced waveforms that helped find the transient detonation effects of the explosive mix under investigation. The three-dimensional effects of converging shock waves, detonation waves, rarefactions, explosive jetting, and the shock-induced change in the index of refraction were considered and quantified in order to produce actual particle velocity and pressure time histories.

Tenths of a kilobar (kbar) were measured with SASN in contact with fused silica windows with PDV and another well-known laser interferometer, velocity interferometry for any reflector (VISAR). This pressure range may be close to the lower limit for fused silica fiber optics. Different applications, however, may utilize different optical materials, such as polymethyl methacrylate (PMMA) for lower pressure regimes, because fused silica is not as sensitive to relatively low pressures. The fused silica fibers allowed measurement of deflagrations and detonations in SASN-based explosives in the range of 0.1-3 kbars. These measures indicated a potential lower pressure range of a properly designed and calibrated sensor system. The upper range is likely around the tensile strength of the fiber material on a timescale that allows sufficiently strong rarefactions to enter the fiber material and fracture it, severing the optical path. A caveat at the upper range is that the read time for the apparent particle velocity will be shorter and shorter as the stress level increases. This will likely mean that a sensor system will become less of a waveform indicator and more of a time of arrival device in this upper regime of pressure.

Figure 11:
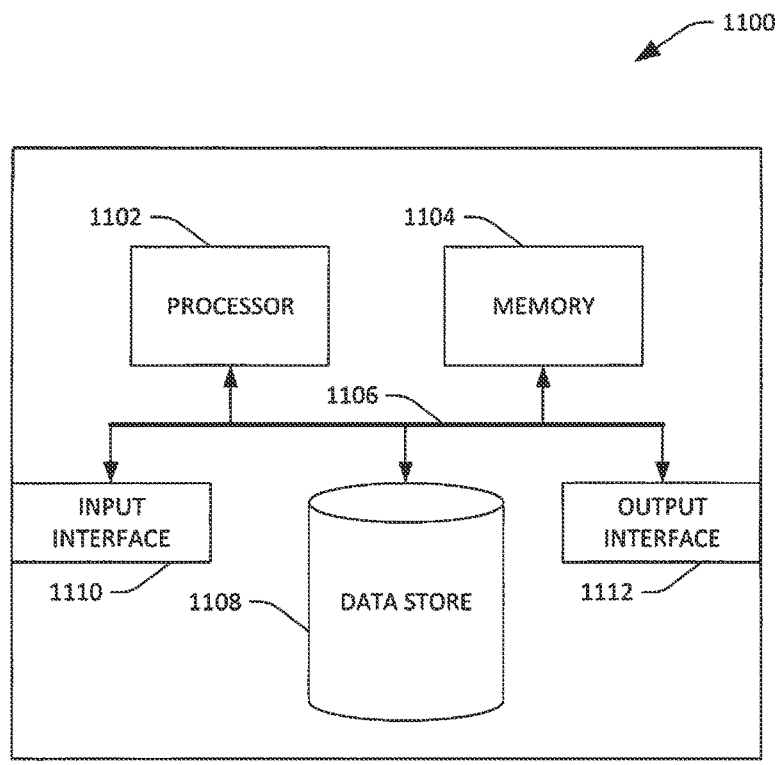
FIG. 11 illustrates an exemplary computing system.

Referring now to FIG. 11, a high-level illustration of an exemplary computing device 1100 that can be used in accordance with the systems and methodologies disclosed herein is illustrated. For instance, the computing device 1100 may be used in a system that is configured to compute values indicative of behaviors of a sample based upon electrical signals received from a detector. By way of another example, the computing device 1100 can be used in a system that is configured to generate graphs that are indicative of behavior of a sample based upon electrical signals output by detectors. The computing device 1100 includes at least one processor 1102 that executes instructions that are stored in a memory 1104. The instructions may be, for instance, instructions for implementing functionality described as being carried out by one or more components discussed above or instructions for implementing one or more of the methods described above. The processor 1102 may access the memory 1104 by way of a system bus 1106. In addition to storing executable instructions, the memory 1104 may also store values indicative of electrical signals output by detectors.

The computing device 1100 additionally includes a data store 1108 that is accessible by the processor 1102 by way of the system bus 1106. The data store 1108 may include executable instructions, values pertaining to electrical signals, etc. The computing device 1100 also includes an input interface 1110 that allows external devices to communicate with the computing device 1100. For instance, the input interface 1110 may be used to receive instructions from an external computer device, from a user, etc. The computing device 1100 also includes an output interface 1112 that interfaces the computing device 1100 with one or more external devices. For example, the computing device 1100 may display text, images, etc. by way of the output interface 1112.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein as being performed by the computing device 116 can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

As used herein, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A sensor system in combination with a sample that is configured to measure a change in a property of reflected light that is indicative of a behavior of the sample, comprising:
a sample that is desirably analyzed; and
an optical fiber comprising:
an inner fiber through which light travels; and
a reflective surface applied to a cleaved tip of the optical fiber configured such that light travelling through the inner fiber is reflected back through the inner fiber by the reflective surface and does not impinge upon the sample, the reflective surface being orthogonal to the inner fiber at the cleaved tip, the cleaved tip of the optical fiber embedded in the sample that is desirably analyzed; and
a detector that is optically coupled to the optical fiber, the detector configured to generate an electrical signal responsive to receiving light reflected by the reflective surface, wherein the electrical signal is indicative of a behavior of the sample.

2. The sensor system of claim 1, wherein the reflective surface is arranged in parallel to an exposed surface of the sample.

3. The sensor system of claim 2, wherein the sample has a thickness defined by the exposed surface and a second surface, the thickness between 100 microns and one millimeter.

4. The sensor system of claim 3, the sample being an explosive.

5. The sensor system of claim 4, the explosive being silver acetylide-silver nitrate.

6. The sensor system of claim 1, further comprising:
a laser interferometer that is optically coupled to the optical fiber, wherein the laser interferometer comprises a laser that is configured to emit light that travels through the inner fiber; and
a computing device that is electrically coupled to the detector, wherein the computing device is configured to receive the electrical signal and output the value that is indicative of the behavior of the sample based upon the electrical signal.

7. The sensor system of claim 6, the behavior of the explosive being detonation velocity of the explosive, the value being an apparent particle velocity of the light.

8. The sensor system of claim 6; further comprising a second optical fiber positioned substantially parallel to the optical fiber the second optical fiber having a second inner fiber and a second reflective surface applied to a cleaved tip of the second optical fiber, the cleaved tip of the second optical fiber embedded in the sample, such that light travelling through the second inner fiber is reflected back through the second inner fiber by the second reflective surface.

9. The sensor system of claim 8, the second reflective surface arranged in parallel with the exposed surface of the sample.

10. The sensor system of claim 9, the reflective surface being embedded a first depth into the sample, the second reflective surface being embedded a second depth into the sample, the first and second depths being different from one another.

11. The sensor system of claim 1, wherein the reflective surface comprises a plurality of layers, wherein the plurality of layers includes a layer of aluminum oxide, a layer of aluminum, and a layer of titanium.

12. The sensor system of claim 11, wherein the layer of aluminum is between the layer of aluminum oxide and the layer of titanium, the layer of titanium being adjacent to the cleaved tip of the optical fiber.

* * * * *